United States Patent
Kobayashi et al.

(10) Patent No.: US 8,579,826 B2
(45) Date of Patent: Nov. 12, 2013

(54) ARTERIOSCLEROSIS DEGREE JUDGMENT DEVICE CAPABLE OF JUDGING ARTERIOSCLEROSIS DEGREE PRECISELY

(75) Inventors: Tatsuya Kobayashi, Otsu (JP); Toshihiko Ogura, Kyoto (JP); Yoshihiko Sano, Kyoto (JP); Toshihiko Abe, Chofu (JP); Takahide Tanaka, Otsu (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 729 days.

(21) Appl. No.: 12/743,074

(22) PCT Filed: Nov. 13, 2008

(86) PCT No.: PCT/JP2008/070671
§ 371 (c)(1),
(2), (4) Date: May 14, 2010

(87) PCT Pub. No.: WO2009/063939
PCT Pub. Date: May 22, 2009

(65) Prior Publication Data
US 2010/0268092 A1  Oct. 21, 2010

(30) Foreign Application Priority Data
Nov. 15, 2007 (JP) ................. 2007-297046

(51) Int. Cl.
*A61B 5/0205* (2006.01)
*A61B 5/022* (2006.01)
*A61B 5/0225* (2006.01)

(52) U.S. Cl.
USPC ............ 600/490; 600/483; 600/485; 600/504

(58) Field of Classification Search
None
See application file for complete search history.

(56) References Cited

U.S. PATENT DOCUMENTS 5,617,868 A * 4/1997 Harada et al. ................. 600/490
2004/0024325 A1 * 2/2004 Nishibayashi et al. ....... 600/492
(Continued)

FOREIGN PATENT DOCUMENTS

CN    1657002 A    8/2005
JP    2000-316821 A    11/2000
(Continued)

OTHER PUBLICATIONS

Chinese Office Action issued in Chinese Application No. 200880116048.1 dated Aug. 3, 2011 and English translation thereof, 12 pages.

(Continued)

*Primary Examiner* — Patricia Mallari
*Assistant Examiner* — Michael J Burrage
(74) *Attorney, Agent, or Firm* — Osha Liang LLP

(57) ABSTRACT

A cuff of a pulse wave meter equipped with an arteriosclerosis degree judgment device has air bags for compressing a living body having a double structure along an artery including an avascularization air bag and a pulse-wave measuring air bag. Provided at outer circumferential sides of these air bags are a curler for integrally pressing these air bags against an upper arm, and an air bag for pressing the curler from the outer circumferential side. A member for suppressing vibrations is provided between a curler-compressing air bag and the pulse-wave measuring air bag, and suppresses propagation of vibrations from the curler-compressing air bag to the pulse-wave measuring air bag. The pulse wave meter measures a pulse wave based on changes in internal pressure in the pulse-wave measuring air bag while the avascularization air bag provides avascularization at the peripheral side.

7 Claims, 13 Drawing Sheets

(56) References Cited

U.S. PATENT DOCUMENTS

| | | | |
|---|---|---|---|
| 2004/0064055 A1* | 4/2004 | Kawaguchi | 600/490 |
| 2005/0015015 A1 | 1/2005 | Mizukoshi et al. | |
| 2005/0182332 A1* | 8/2005 | Sano et al. | 600/499 |

FOREIGN PATENT DOCUMENTS

| | | | |
|---|---|---|---|
| JP | 2004-113593 A | 4/2004 | |
| JP | 2004-321251 A | 11/2004 | |
| JP | 2005-230175 A | 9/2005 | |
| JP | 2007-044362 A | 2/2007 | |
| JP | 2007-125247 A | 5/2007 | |
| RU | 2093077 C1 | 10/1997 | |
| SU | 1467429 A1 | 3/1989 | |

OTHER PUBLICATIONS

English Abstract of CN 1657002-A published on Aug. 24, 2005, 1 page.

Notice of Allowance for Russian Patent Application No. 2010123931, mailed on Nov. 11, 2011, and English translation thereof, 16 pages.

Espacenet Patent Abstract, Application No. SU 1467429, dated Mar. 23, 1989, 1 page.

Abstract of JP2004-113593; data supplied from the esp@cenet database—Worldwide, 1 page.

Abstract of JP2005-230175; data supplied from the esp@cenet database—Worldwide, 1 page.

Abstract of JP2004-321251; data supplied from the esp@cenet database—Worldwide, 1 page.

Abstract of JP2007-125247; data supplied from the esp@cenet database—Worldwide, 1 page.

Abstract of JP2007-044362; data supplied from the esp@cenet database—Worldwide, 1 page.

Abstract of JP2000-316821; data supplied from the esp@cenet database—Worldwide, 1 page.

International Search Report issued in PCT/JP2008/070671, mailed on Dec. 9, 2008, with translation, 4 pages.

* cited by examiner

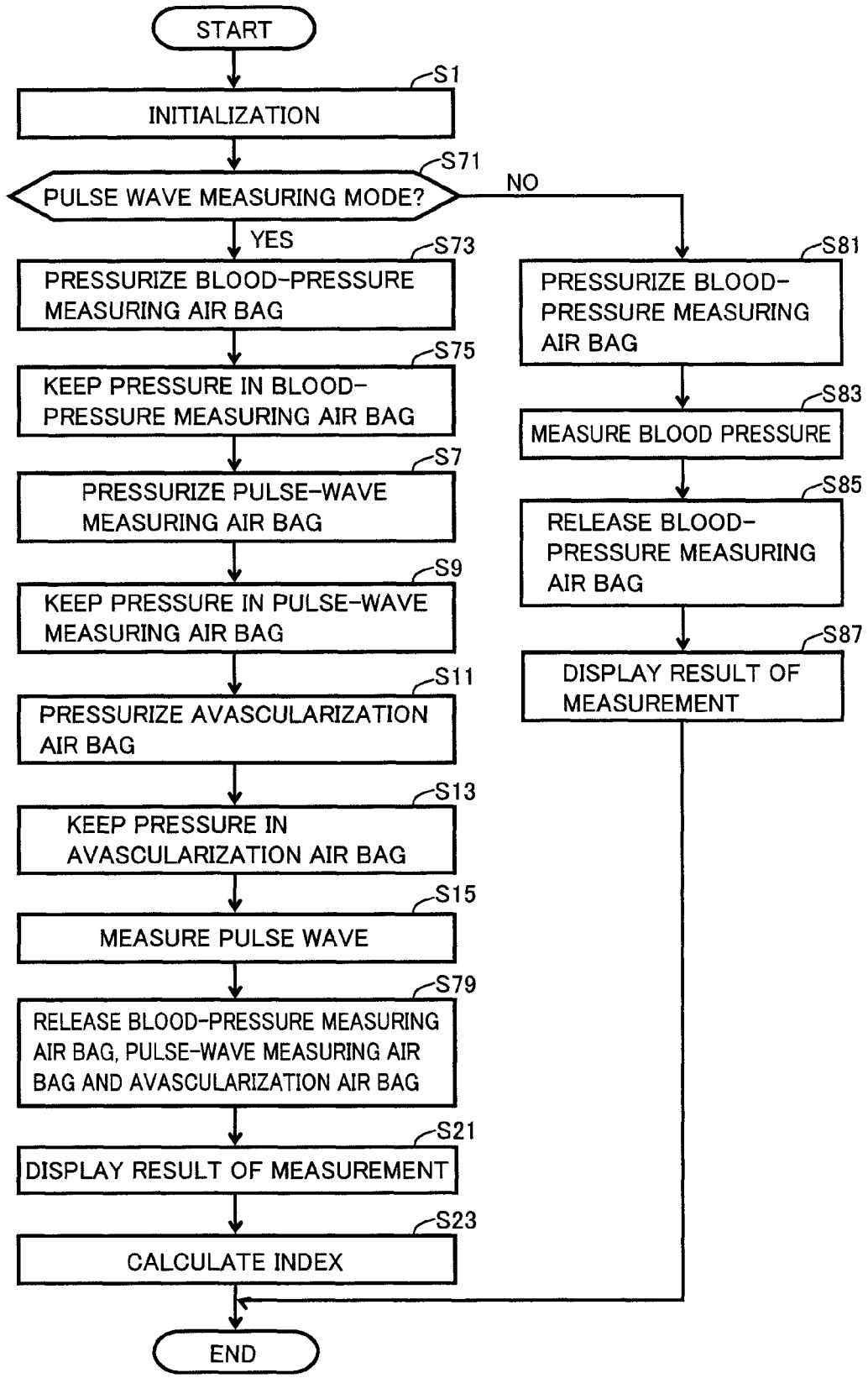

ARTERIOSCLEROSIS DEGREE JUDGMENT DEVICE CAPABLE OF JUDGING ARTERIOSCLEROSIS DEGREE PRECISELY

TECHNICAL FIELD

The present invention relates to a device for judging a degree of arteriosclerosis, and more particularly to a device for analyzing a pulse wave to attain an index for judging a degree of arteriosclerosis, and judging a degree of arteriosclerosis using the index.

BACKGROUND ART

As a conventional device for judging a degree of arteriosclerosis, Japanese Patent Laying-Open No. 2000-316821 (hereinafter referred to as Patent Document 1), for example, discloses a device for judging a degree of arteriosclerosis by checking a velocity that a pulse wave ejected from the heart propagates (hereinafter referred to as PWV: pulse wave velocity). Since the pulse wave velocity increases as arteriosclerosis progresses, PWV serves as an index for judging a degree of arteriosclerosis. By applying cuffs or the like for measuring pulse waves to at least two locations, such as an upper arm and a lower extremity, and measuring pulse waves simultaneously, PWV is calculated from the difference between time points at which the respective pulse waves appear and from the length of an artery between the two locations to which the cuffs or the like for measuring pulse waves are applied. PWV differs in value according to measurement sites. A typical PWV includes baPWV in the case where measurement sites are an upper arm and an ankle, and cfPWV in the case where measurement sites are the carotid artery and the iliac artery.

As a technique for judging a degree of arteriosclerosis from an upper arm's pulse wave, Japanese Patent Laying-Open No. 2007-44362 (hereinafter referred to as Patent Document 2) discloses a technique for providing a double structure including a blood-pressure measuring cuff and a pulse-wave measuring cuff.

Japanese Patent Laying-Open No. 2004-113593 (hereinafter referred to as Patent Document 3) discloses a technique for separating an ejected pulse wave ejected from the heart and reflected waves from the branch of the iliac artery and a hardened portion in an artery, to thereby judge a degree of arteriosclerosis based on the difference and ratio between their amplitudes, the difference between time points of appearance, and the like.

Patent Document 1: Japanese Patent Laying-Open No. 2000-316821
Patent Document 2: Japanese Patent Laying-Open No. 2007-44362
Patent Document 3: Japanese Patent Laying-Open No. 2004-113593
Patent Document 4: Japanese Patent Laying-Open No. 2005-230175

DISCLOSURE OF THE INVENTION

Problems to be Solved by the Invention

To measure PWV using the device disclosed in Patent Document 1, cuffs or the like need to be applied to at least two locations, such as an upper arm and a lower extremity, as described earlier. This arises a problem in that it is difficult to measure PWV easily at home even with the device disclosed in Patent Document 1.

In contrast, Patent Document 2 discloses the technique for judging a degree of arteriosclerosis from an upper arm's pulse wave. However, the device disclosed in Patent Document 2 is configured to have the double structure including the blood-pressure measuring cuff and the pulse-wave measuring cuff. With the pulse-wave measuring cuff alone, a reflected wave may not be separated accurately, since a reflex from a periphery or the like has been superimposed. This arises a problem in that it is difficult to judge a degree of arteriosclerosis precisely.

Patent Document 3 discloses judging a degree of arteriosclerosis upon separating an ejected wave and a reflected wave from a measured wave, however, a prerequisite pulse wave measurement has a problem in that a pulse wave cannot be measured stably depending on how a cuff is wrapped, such as when the applied position of the cuff or the like for measuring a pulse wave is displaced, or when the cuff or the like is wrapped loosely. As a technique for stabilizing wrapping of a cuff, there is a technique for automatically wrapping a cuff. As a technique for automatically and stably wrapping a cuff, Japanese Patent Laying-Open No. 2005-230175 (hereinafter referred to as Patent Document 4), for example, discloses a technique for automatic wrapping by means of an air bag. However, a problem arises in that noise occurred in the air bag is transferred to a pulse-wave cuff or vibrations for keeping the air bag at a constant pressure are transferred to the pulse-wave cuff, causing an error to occur when calculating a degree of arteriosclerosis from a pulse wave obtained by the pulse-wave cuff.

The present invention has been made to solve the above-described problems, and has an object to provide a device configured such that a cuff or the like for measuring a pulse wave can be wrapped stably, to thereby measure a pulse wave precisely at a single measurement site and calculate an index for judging a degree of arteriosclerosis based on that pulse wave.

Means for Solving the Problems

To accomplish the above-described object, according to an aspect of the present invention, an arteriosclerosis degree judgment device includes a first fluid bag to be wrapped around a measurement site at a central side thereof and a second fluid bag to be wrapped around the measurement site at a peripheral side thereof, a compression member located at outer circumferential sides of both of the first fluid bag and the second fluid bag to oppose to the measurement site, for integrally covering both of the first fluid bag and the second fluid bag, a first sensor for measuring an internal pressure in the first fluid bag, an adjustment unit for adjusting a pressure force of the compression member, a detection unit for detecting a pulse wave at the measurement site based on a change in an internal pressure in the first fluid bag, and a calculation unit for analyzing the pulse wave to calculate an index for judging a degree of arteriosclerosis. The adjustment unit causes the compression member to pressurize both of the first fluid bag and the second fluid bag so as to be compressed against the measurement site. The first fluid bag and the second fluid bag are pressed against the measurement site with a certain pressure force. The detection unit detects the pulse wave at the measurement site based on a change in the internal pressure in the first fluid bag while being pressed against the measurement site with the certain pressure force.

Effects of the Invention

The application of the device according to the present invention can facilitate a stable pulse wave measurement to judge a degree of arteriosclerosis and the like precisely.

BRIEF DESCRIPTION OF THE DRAWINGS

FIG. 15 is a flow chart showing another specific example of a measuring operation at the pulse wave meter.

Figure 1:
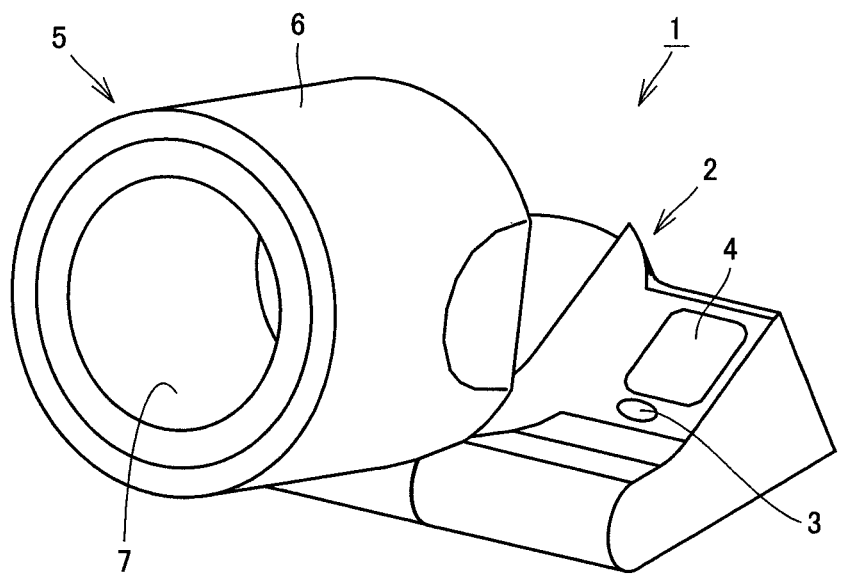
FIG. 1 is a perspective view showing a specific example of an appearance of a pulse wave meter according to an embodiment.

DESCRIPTION OF THE REFERENCE SIGNS 1 pulse wave meter; 2 base; 3 operating unit; 4 display unit; 5 measuring unit; 6 housing; 7 cover; 8, 13A, 13B, 85 air bag; 10 curler; 13C member; 20A, 20B, 30 air system; 21A, 21B, 31 air pump; 22A, 22B, 32 air valve; 23A, 23B, 33 pressure sensor; 26A, 26B, 27A, 27B, 36, 37 driving circuit; 28A, 28B, 38 amplifier; 29A, 29B, 39 A/D converter; 40 CPU; 41 memory unit; 50 orifice; 51 adjusting unit; 81 artificial muscle; 83 control circuit; 100 upper arm.

BEST MODES FOR CARRYING OUT THE INVENTION

Embodiments of the present invention will now be described with reference to the drawings. The same or corresponding elements have the same reference characters allotted. They also have the same names and functions.

Figure 2:
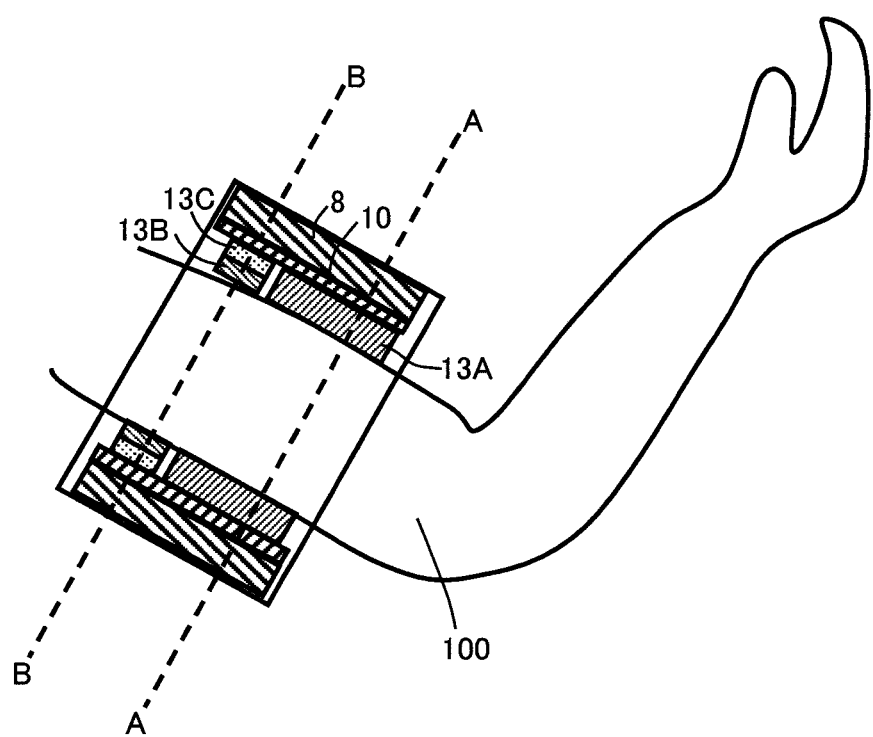
FIG. 2 is a schematic sectional view showing a measuring posture when measuring a pulse wave using the pulse wave meter according to the embodiment.

FIG. 1 is a perspective view showing a specific example of an appearance of a pulse wave meter including an arteriosclerosis degree judgment device according to an embodiment of the present invention. FIG. 2 is a schematic sectional view showing a measuring posture when measuring a pulse wave using the pulse wave meter shown in FIG. 1.

As shown in FIG. 1, a pulse wave meter 1 equipped with the arteriosclerosis degree judgment device according to the present embodiment mainly includes a base 2 mounted on a mounting stage such as a table, and a measuring unit 5 through which an upper arm which is a measurement site is inserted. Provided on base 2 are an operating unit 3 where a power button used for power-on, a measurement button for starting a measuring operation and the like are disposed, as well as a display unit 4 for displaying a result of measurement, operation guidance and the like. Measuring unit 5 is attached to base 2 so as to be turned freely, and includes a housing 6 which is a cylindrical frame as well as a holding device housed in an inner circumferential part of housing 6 for compressing and holding a living body. As shown in FIG. 1, in a normal usage condition, the holding device housed in the inner circumferential part of housing 6 is unexposed, and is covered by cover 7.

When measuring a pulse wave using the above-described pulse wave meter 1, as shown in FIG. 2, an upper arm 100 is inserted into a hole located at the inner side of housing 6, and is compressed and held by the holding device incorporated in the inner circumferential part of housing 6, thereby measuring a pulse wave.

With reference to FIG. 2, the holding device incorporated in the inner circumferential part of housing 6 mainly includes air bags 13A and 13B serving as fluid bags for compressing the living body, a curler 10 which is located at outer circumferential sides of these air bags for integrally covering air bags 13A and 13B and which is a generally cylindrical flexible member that is extendable in the radial direction, and an air bag 8 which is a fluid bag located at an outer circumferential side of curler 10 (opposite to the living body) and which inflates to press the outer circumferential surface of curler 10 toward the inner side (toward the living body) so as to reduce curler 10 in diameter, and which covers curler 10 integrally for compressing a flexible member that presses air bags 13A and 13B against the living body from the outer side of curler 10. A member 13C for suppressing vibrations is provided between air bag 13B and curler 10.

Figure 3:
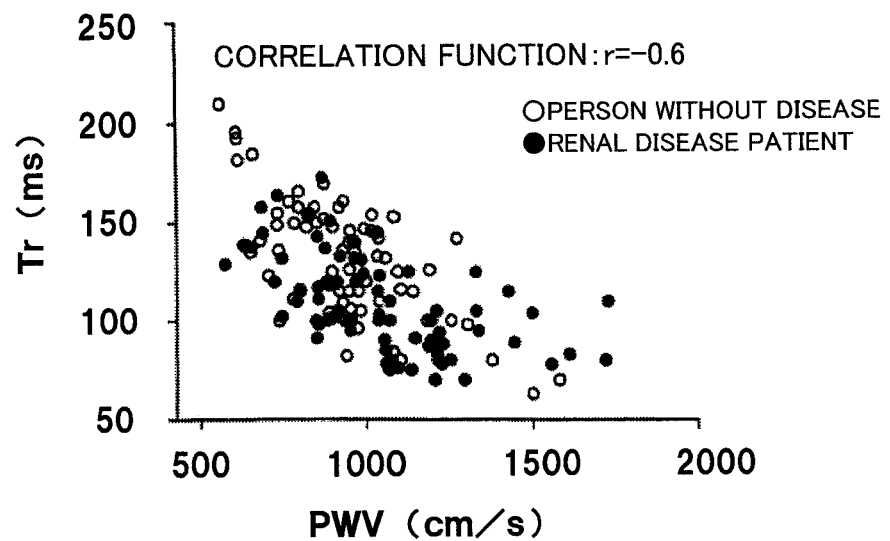
FIG. 3 shows a specific example of a correlation of PWV with a time difference Tr between an ejected wave and a reflected wave.

Pulse wave meter 1 according to the present embodiment attains an index for judging a degree of arteriosclerosis, based on a pulse waveform obtained at a single measurement site. According to the present embodiment, time difference Tr between an ejected wave and a reflected wave is obtained as an index for judging a degree of arteriosclerosis. In the case where the measurement site is an upper arm, and when the reflected wave is a reflected wave from the ankle as a periphery, a correlation between time difference Tr and baPWV which is PWV when measurement sites are an upper arm and an ankle is attained statistically as shown in FIG. 3, for example, by obtaining personal parameters such as age, sex and the like. Accordingly, time difference Tr between an ejected wave and a reflected wave can be used as an index for judging a degree of arteriosclerosis.

Figure 4:
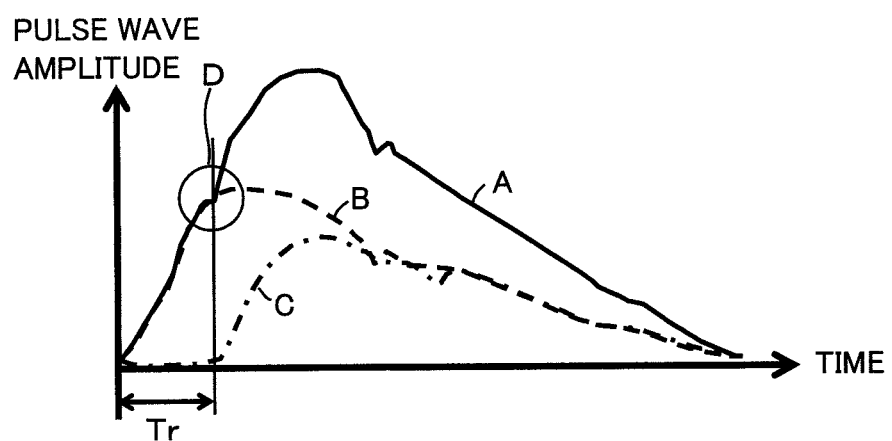
FIG. 4 explains a relationship among a measured pulse waveform, an ejected wave and a reflected wave.

FIG. 4 shows the principles of attaining an index for judging a degree of arteriosclerosis based on a pulse waveform obtained at a single measurement site, and explains a relationship among a measured pulse waveform, an ejected wave and a reflected wave. In FIG. 4, a waveform A indicated by the solid line represents a measured pulse waveform. A waveform B indicated by the broken line represents an ejected wave, and a waveform C indicated by the dashed line represents a reflected wave. As shown in FIG. 4, pulse waveform A obtained by a measurement is a synthetic wave of ejected wave B and reflected wave C. An arrival of the reflected wave to the measurement site is detected as an inflection point D on pulse waveform A. The above-mentioned time difference Tr is thus obtained as a time duration from a rising edge of pulse waveform A to inflection point D.

To obtain inflection point D from pulse waveform A obtained by a measurement, a precise pulse waveform needs to be obtained. Therefore, an air bag of pulse wave meter 1 according to the present embodiment exhibits a double structure along an artery including air bags 13A and 13B. Air bag 13A is disposed at a peripheral side (distant from the heart) of upper arm 100, while air bag 13B is disposed at a central side (closer to the heart). After upper arm 100 is compressed and held, air bags 13A and 13B inflate and deflate. Inflation of air bag 13A produces avascularization at the peripheral side of the artery. Inflation of air bag 13B in this state allows detection of an artery pressure pulse wave appearing in the artery in the avascularization. That is, a pulse wave measurement can be performed with avascularization provided at the peripheral side. This allows a pulse wave to be measured precisely. As a result, the above-mentioned inflection point D can be obtained precisely from measured pulse waveform A, to thereby obtain time difference Tr. Accordingly, baPWV can be obtained precisely using the correlation as shown in FIG. 3.

Figure 5A:
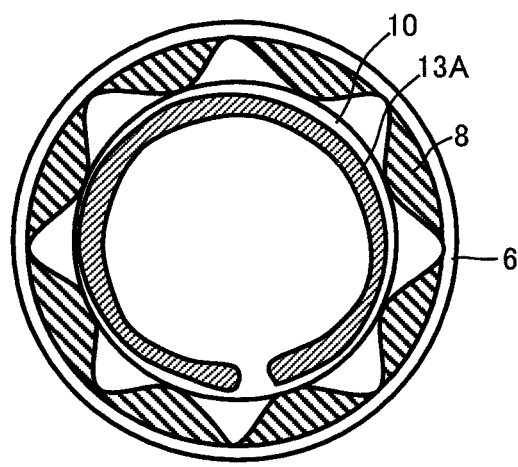
FIG. 5A is a schematic sectional view for explaining an internal structure of a measuring unit of the pulse wave meter according to the embodiment.
Figure 5B:
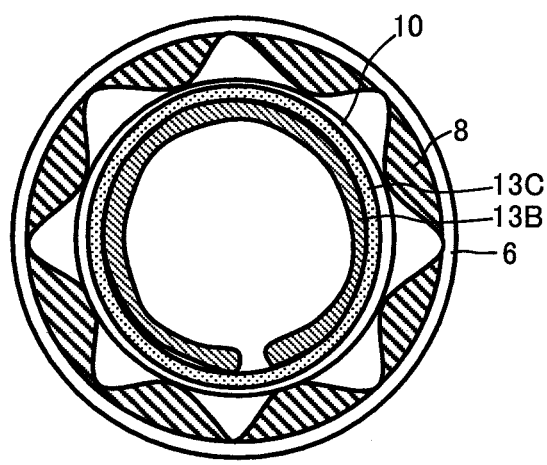
FIG. 5B is a schematic sectional view for explaining an internal structure of the measuring unit of the pulse wave meter according to the embodiment.

FIGS. 5A and 5B are schematic sectional views for explaining an internal structure of measuring unit 5 of pulse wave meter 1 according to the present embodiment. FIG. 5A schematically shows a section taken along a line A-A of FIG. 2, and FIG. 5B schematically shows a section taken along a line B-B of FIG. 2.

With reference to FIGS. 5A and 5B, air bag 8 is disposed at the inner side of housing 6. Air bag 8 can inflate and deflate so as to vary in volume, by the action of an air system 30 (see FIG. 6) for compressing curler 10 which will be described later. Curler 10 made of a plate-like member curled in a generally cylindrical manner is located at the inner side of air bag 8. Curler 10 is made of a resin material such as polypropylene resin, and has a notch extending in the axial direction located at a predetermined position in the circumferential direction. This notch allows curler 10 to be elastically deformed so as to expand and contract in the radial direction through the application of external force. More specifically, curler 10 is deformed in the radial direction under the action of external force, and returns to an original state with no external force being applied. Curler 10 has its opposite ends in the circumferential direction formed to partially overlap each other with no external force being applied. This prevents the opposite ends of curler 10 from interfering with each other during contraction, so that the contraction is not hindered.

As described earlier, curler 10 is located at the outer circumferential sides of air bags 13A and 13B, and is sized to cover both of air bags 13A and 13B. Reduction in diameter of curler 10 by air bag 8 causes both of air bags 13A and 13B to be pressed against the living body.

More specifically, with respect to the section taken along the line A-A in FIG. 2, that is, the section at a position where air bag 13A is disposed at the peripheral side of upper arm 100, air bag 13A is located at the inner side of curler 10, with reference to FIG. 5A. Air bag 13A can inflate and deflate so as to vary in volume, by the action of an air system 20A (see FIG. 6) for compressing the living body which will be described later.

Also, more specifically, with respect to the section taken along the line B-B in FIG. 2, that is, the section at a position where air bag 13B is disposed at the central side of upper arm 100, air bag 13B is located at the inner side of curler 10 with member 13C interposed therebetween, with reference to FIG. 5B. Air bag 13B can inflate and deflate so as to vary in volume, by the action of an air system 20B (see FIG. 6) for compressing the living body which will be described later. Member 13C is a member for suppressing propagation of vibrations from curler 10 to air bag 13B. Preferably, member 13C interrupts propagation of vibrations from curler 10 to air bag 13B. Member 13C has a thickness of approximately several millimeters (1 to 2 mm), and is sized so as to cover at least part of a contact surface between curler 10 and air bag 13B and not to reach air bag 13A. Preferably, member 13C has the same size as air bag 13B. Member 13C is made of a material that absorbs vibrations to suppress propagation of the vibrations, such as resin, foam resin or foam rubber. Member 13C is suitably embodied by a gel sheet material, a rubber plate or the like.

As described above, pulse wave meter 1 according to the present embodiment exhibits a double structure along an artery in which the air bag for compressing the living body includes air bags 13A and 13B, and further exhibits a triple structure of air bags in which air bag 8 for pressing curler 10 that integrally pressurizes air bags 13A and 13B is provided at the outer circumferential sides of air bags 13A and 13B. Air bags 13A and 13B are thereby pressed evenly against upper arm 100 which is a measurement site. An examinee can therefore put on air bags 13A and 13B stably. As a result, a pulse wave can be measured precisely.

Due to variations in volume of air bag 13A by the action of air system 20A, vibrations propagate from air bag 13A to curler 10 and air bag 8. As described earlier, each of curler 10 and air bag 8 integrally covers both of air bags 13A and 13B, and serves as a compression member for compressing air bags 13A and 13B. Accordingly, when vibrations occurred at curler 10 and air bag 8 due to vibrations of air bag 13A propagate to air bag 13B, the precision of pulse wave measurement will be affected. Therefore, pulse wave meter 1 according to the present embodiment includes member 13C for preventing vibrations occurred at curler 10 and air bag 8 from propagating to air bag 13B.

First Embodiment

Figure 6:
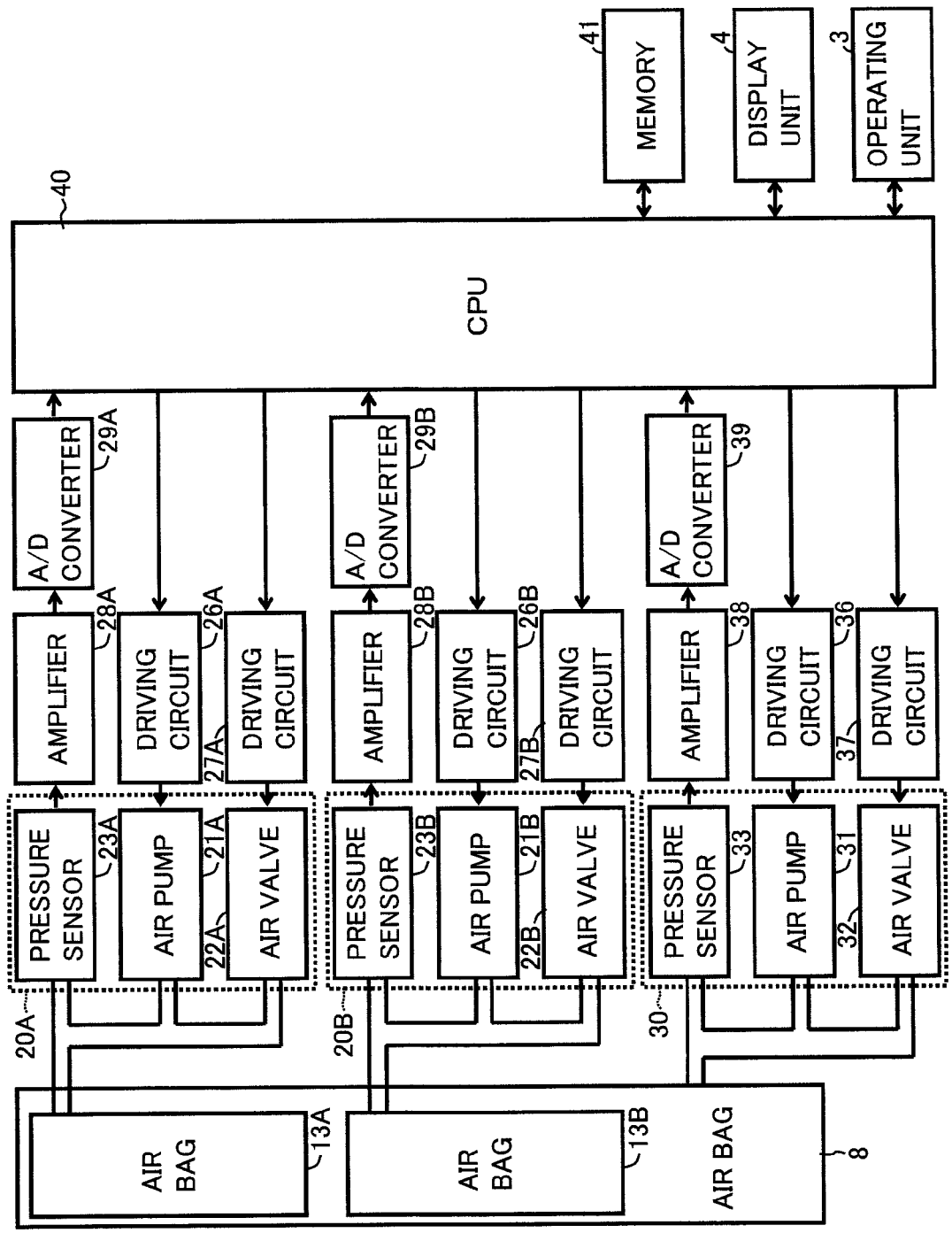
FIG. 6 is a functional block diagram of a pulse wave meter according to a first embodiment.

FIG. 6 is a functional block diagram of pulse wave meter 1 according to a first embodiment. With reference to FIG. 6, pulse wave meter 1 according to the first embodiment includes air system 20A connected to air bag 13A with an air tube, air system 20B connected to air bag 13B with an air tube, and air system 30 connected to air bag 8 with an air tube, as well as a CPU (Central Processing Unit) 40 for controlling their operations.

Air system 20A includes an air pump 21A, an air valve 22A and a pressure sensor 23A. Similarly, air system 20B includes an air pump 21B, an air valve 22B and a pressure sensor 23B.

Air pump 21A is means for pressurizing air bag 13A. Air pump 21B is means for pressurizing air bag 13B. They are driven by driving circuits 26A and 26B having received commands from CPU 40, respectively, to pump compressed air into air bags 13A and 13B such that pressures therein become predetermined pressures during a measurement.

Air valves 22A and 22B are means for maintaining and reducing pressures in air bags 13A and 13B, respectively. Air valves 22A and 22B are controlled to be opened/closed by driving circuits 27A and 27B having received commands from CPU 40, respectively. By controlling air valves 22A and 22B to be opened/closed, pressures in air bags 13A and 13B having been increased by air pumps 21, respectively, during a measurement are maintained and reduced. After the measurement is terminated, the pressures in air bags 13A and 13B are returned to atmospheric pressure.

Pressure sensors 23A and 23B are means for detecting the pressures in air bags 13A and 13B, respectively. Pressure sensors 23A and 23B detect pressures in air bags 13A and 13B that vary with time during a measurement, and output signals in accordance with detected values to amplifiers 28A and 28B, respectively. Amplifiers 28A and 28B amplify the signals received from pressure sensors 23A and 23B for output to A/D converters 29A and 29B, respectively. A/D converters 29A and 29B digitize analog signals received from amplifiers 28A and 28B for output to CPU 40, respectively.

Air system 30 includes an air pump 31, an air valve 32 and a pressure sensor 33. Air pump 31 is means for pressurizing air bag 8. Air pump 31 is driven by a driving circuit 36 having received a command from CPU 40 to pump compressed air into air bag 8 such that a pressure therein becomes a predetermined pressure at the start of measurement.

Air valve 32 is means for maintaining and reducing the pressure in air bag 8. Air valve 32 is controlled to be opened/closed by a driving circuit 37 having received a command from CPU 40. Controlling air valve 32 to be opened/closed allows the pressure in air bag 8 having been increased by air pump 31 during a measurement to be maintained. After the measurement is terminated, the pressure in air bag 8 is returned to atmospheric pressure.

Pressure sensor 33 is means for detecting the pressure in air bag 8. Pressure sensor 33 detects the pressure in air bag 8 at the start of measurement, and outputs a signal in accordance with a detected value to an amplifier 38. Amplifier 38 amplifies the signal received from pressure sensor 33 for output to A/D converter 39. A/D converter 39 digitizes an analog signal received from amplifier 38 for output to CPU 40.

CPU 40 controls air systems 20A, 20B and 30 based on commands input to operating unit 3 provided on base 2 of the pulse wave meter, and outputs the result of measurement to display unit 4 and memory unit 41. Memory unit 41 is means for storing the result of measurement, and also for storing programs to be executed by CPU 40.

Figure 7:
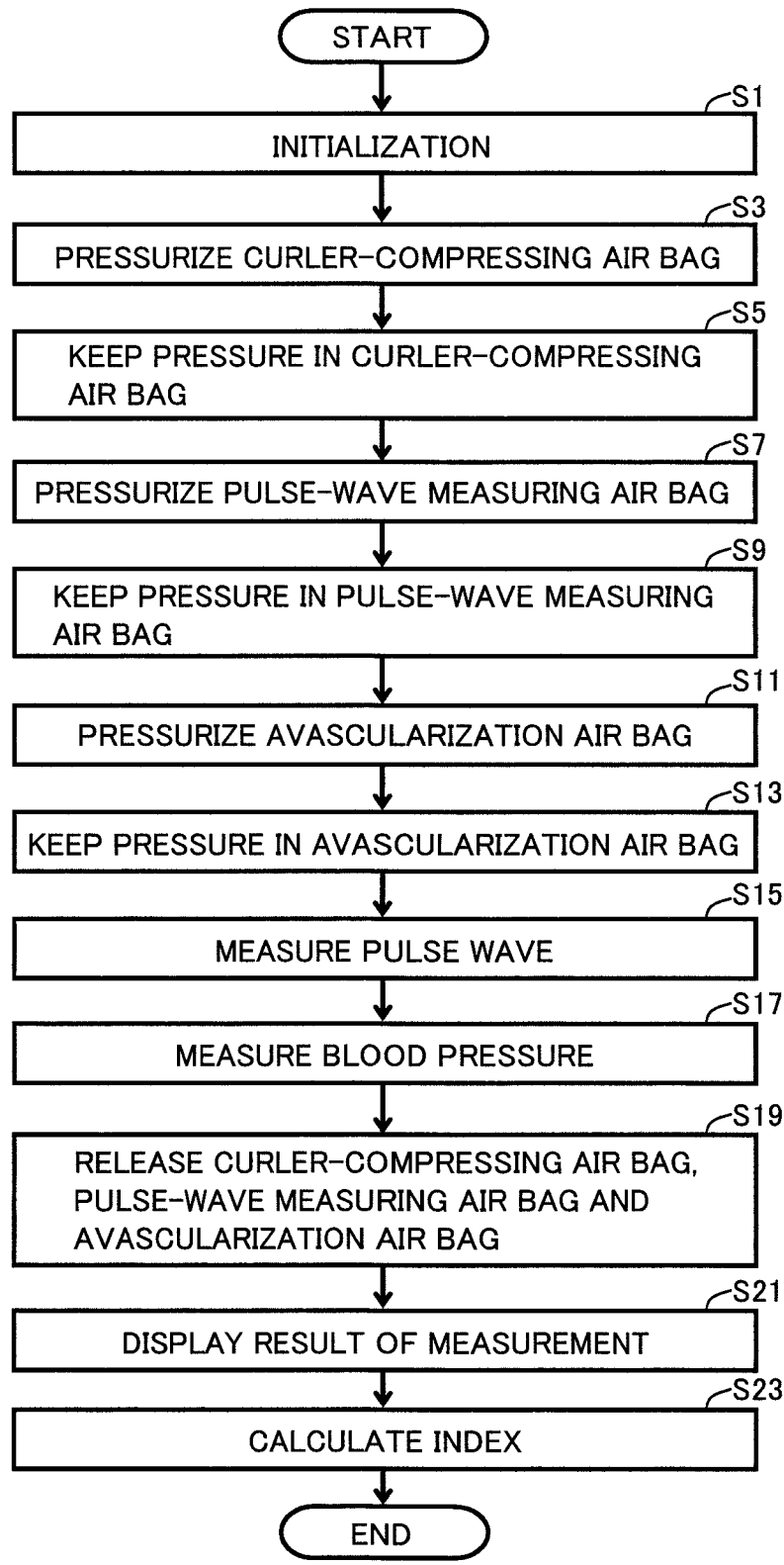
FIG. 7 is a flow chart showing a measuring operation at the pulse wave meter according to the first embodiment.

FIG. 7 is a flow chart showing a measuring operation at pulse wave meter 1 according to the first embodiment. The operation shown in FIG. 7 is started by an examinee or the like pressing the measurement button provided on operating unit 3 on base 2, and is implemented by CPU 40 reading out the programs stored in memory unit 41 to control the respective units shown in FIG. 6.

Figure 8:
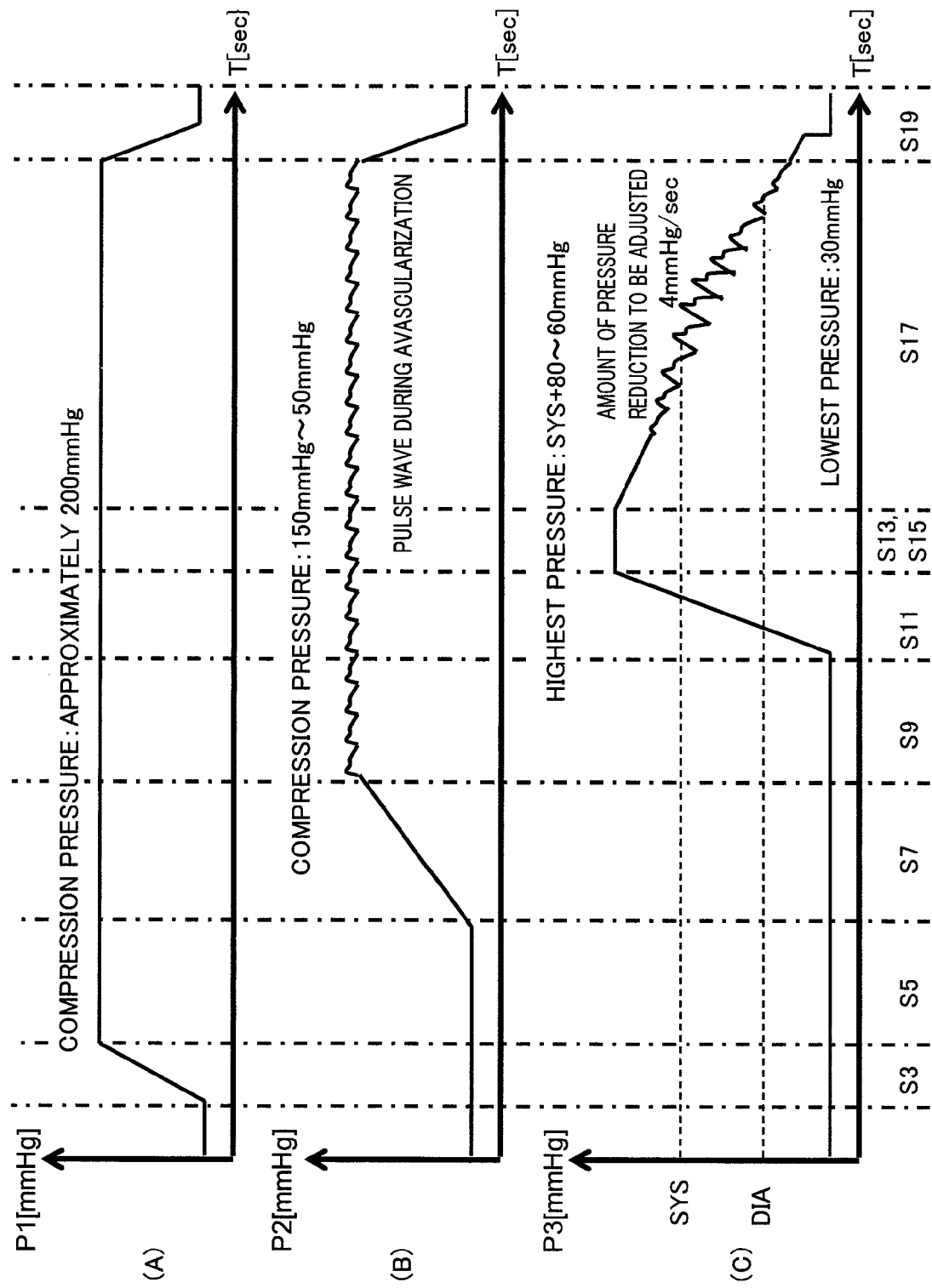
FIG. 8 shows changes in pressure in each air bag during the measuring operation at the pulse wave meter.

FIG. 8 shows changes in pressure in each air bag during the measuring operation at pulse wave meter 1. FIG. 8 shows, at (A), changes with time in a pressure P1 in air bag 8, which are equivalent to changes in pressure applied to curler 10. FIG. 8 also shows, at (B), changes with time in a pressure P2 in air bag 13B, and at (C), changes with time in a pressure P3 in air bag 13A. S3 to S19 added to the time axis at (A) to (C) in FIG. 8 correspond to the respective steps of the measuring operation at pulse wave meter 1 which will be described later.

With reference to FIG. 7, when the operation is started, initialization of the respective units is performed first by CPU 40 (step S1). CPU 40 then outputs a control signal to air system 30 to pressurize air bag 8 (step S3). Pressurization of air bag 8 at step S3 is performed based on a pressure signal from pressure sensor 33 until the pressure in air bag 8 reaches a predetermined pressure. In the example shown at (A) in FIG. 8, the predetermined pressure is approximately 200 mmHg, for example. Having reached the predetermined pressure, CPU 40 terminates the pressurization of air bag 8 at that time point, and causes the predetermined pressure to be maintained such the pressure in air bag 8 is kept at that pressure (step S5). In the example shown at (A) in FIG. 8, pressure P1 in air bag 8 increases at step S3 to approximately 200 mmHg which is the predetermined pressure, and is maintained at that pressure at and after step S5.

Then, CPU 40 outputs a control signal to air system 20B to pressurize air bag 13B (step S7). Pressurization of air bag 13B at step S7 is also performed based on a pressure signal from pressure sensor 23B until the pressure in air bag 13B reaches a predetermined pressure. In the example shown at (B) in FIG. 8, the predetermined pressure is approximately 50 to 150 mmHg, for example. Having reached the predetermined pressure, CPU 40 terminates the pressurization of air bag 13B at that time point, and causes the predetermined pressure to be maintained such the pressure in air bag 13B is kept at that pressure (step S9). In the example shown at (B) in FIG. 8, pressure P2 in air bag 13B increases at step S7 to approximately 50 to 150 mmHg which is the predetermined pressure, and is maintained at that pressure at and after step S9.

Then, CPU 40 outputs a control signal to air system 20A to pressurize air bag 13A (step S11). Pressurization of air bag 13A at step S11 is also performed based on a pressure signal from pressure sensor 23A until the pressure in air bag 13A reaches a predetermined pressure. In the example shown at (C) in FIG. 8, the predetermined pressure is higher, by approximately 60 to 80 mmHg, than a systolic blood pressure (SYS) temporarily set based on changes in an artery pressure pulse wave during the pressurization. Having reached the predetermined pressure, CPU 40 terminates the pressurization of air bag 13A at that time point, and causes the predetermined pressure to be maintained such that the pressure in air bag 13A is kept at that pressure (step S13). With the predetermined pressure being maintained, CPU 40 causes a pulse wave to be measured based on the pressure signal from pressure sensor 23B (step S15). That is, the pulse wave is measured based on changes in internal pressure in air bag 13B. In the example shown at (C) in FIG. 8, pressure P3 in air bag 13A increases at step S11 to a pressure higher than the temporarily set systolic blood pressure (SYS) by approximately 60 to 80 mmHg, and is maintained at that pressure at steps S13 and S15. At this stage, pressure P2 in air bag 13B is maintained as shown at (B) in FIG. 8.

Then, CPU 40 outputs a control signal to air system 20A, so that an artery pressure pulse wave is detected based on the pressure signal from pressure sensor 23A while gradually reducing the pressure in air bag 13A. Then, blood pressure values (systolic blood pressure (SYS) and diastolic blood pressure (DIA)) are calculated based on detected data of the artery pressure pulse wave (step S17). That is, the blood pressure values are calculated based on changes in internal pressure in air bag 13A. In the example shown at (C) in FIG. 8, blood pressure values (systolic blood pressure (SYS) and diastolic blood pressure (DIA)) are calculated while pressure P3 in air bag 13A is gradually reduced at step S17 from the pressure higher than the temporarily set systolic blood pressure (SYS) by approximately 60 to 80 mmHg. Herein, an adjusted amount of pressure reduction is approximately 4 mmHg/sec, for example.

Then, CPU 40 outputs control signals to air systems 20A, 20B and 30, so that the pressures in air bags 13A, 13B and 8 are released to atmospheric pressure (step S19). In the examples shown at (A) to (C) in FIG. 8, pressures P1 to P3 in air bags 13A, 13B and 8 are rapidly reduced to atmospheric pressure at step S21.

Then, CPU 40 performs processing for causing display unit 4 provided on base 2 to display the result of measurement, including the calculated systolic blood pressure (SYS), diastolic blood pressure (DIA), the measured pulse wave, and the like, so that the result of measurement is displayed (step S21). CPU 40 also calculates time difference Tr between an ejected wave and a reflected wave, as the aforementioned index for judging a degree of arteriosclerosis, from the pulse waveform obtained at step S15 (step S23). A calculating technique at step S23 is not specifically limited in the present invention. Time difference Tr between an ejected wave and a reflected wave can be attained by, for example, computing a multi-order derivative (e.g., quartic derivative) of the obtained pulse waveform to obtain the aforementioned inflection point D, and reading out a time duration from the rising edge of the obtained pulse waveform to inflection point D.

In the above-described measuring operation, air bag 13A is used both for avascularization and for calculating blood pressure values, so that the blood pressure values are calculated based on changes in internal pressure in air bag 13A, and the pulse wave is measured based on changes in internal pressure in air bag 13B. However, air bag 13A may be used merely for avascularization, and the blood pressure values may be calculated based on changes in internal pressure in air bag 13B.

By configuring pulse wave meter 1 according to the present embodiment to include member 13C as described above, a precise pulse wave can be measured. As a result, an index for judging a degree of arteriosclerosis can be attained at a single measurement site.

It is to be noted that member 13C is also provided similarly for pulse wave meter 1 according to the second to fourth embodiments which will be described later.

[Modification]

Since curler 10 and air bag 8 each cover both of air bags 13A and 13B integrally as described earlier, vibrations of air bag 13A or the like may lead to vibrations (noise) at curler 10 and air bag 8. Such noise, if occurred during the above-described pulse wave measurement at step S15, will affect the precision of pulse wave measurement. Accordingly, as a modification, CPU 40 causes the pressure in air bag 8 to be adjusted upon detection of the occurrence of noise in the pressure in air bag 8 during a pulse wave measurement, thereby canceling out the occurred noise.

Figure 9:
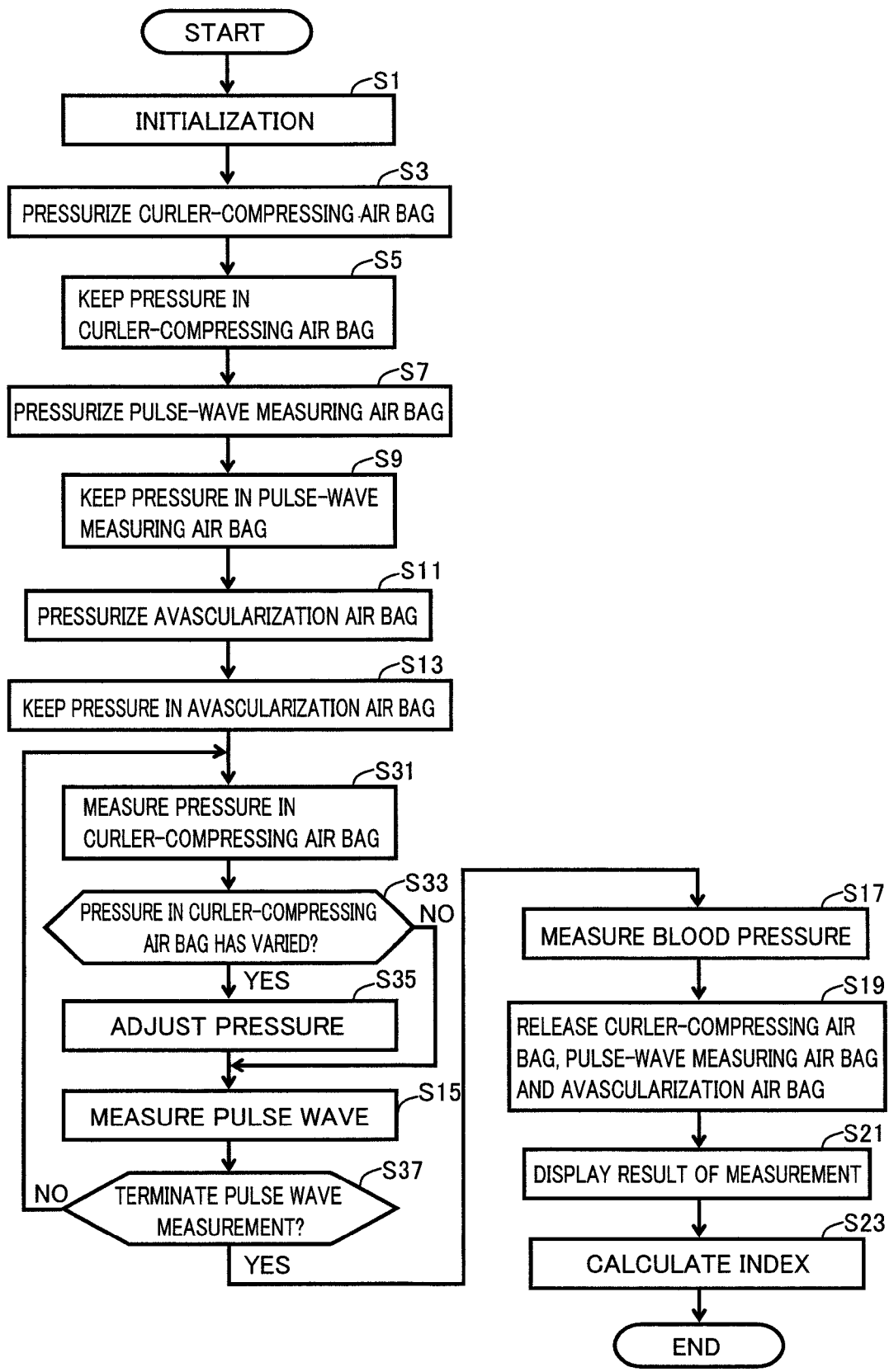
FIG. 9 is a flow chart showing a measuring operation including a pressure adjusting step according to a modification at the pulse wave meter of the first embodiment.
Figure 10:
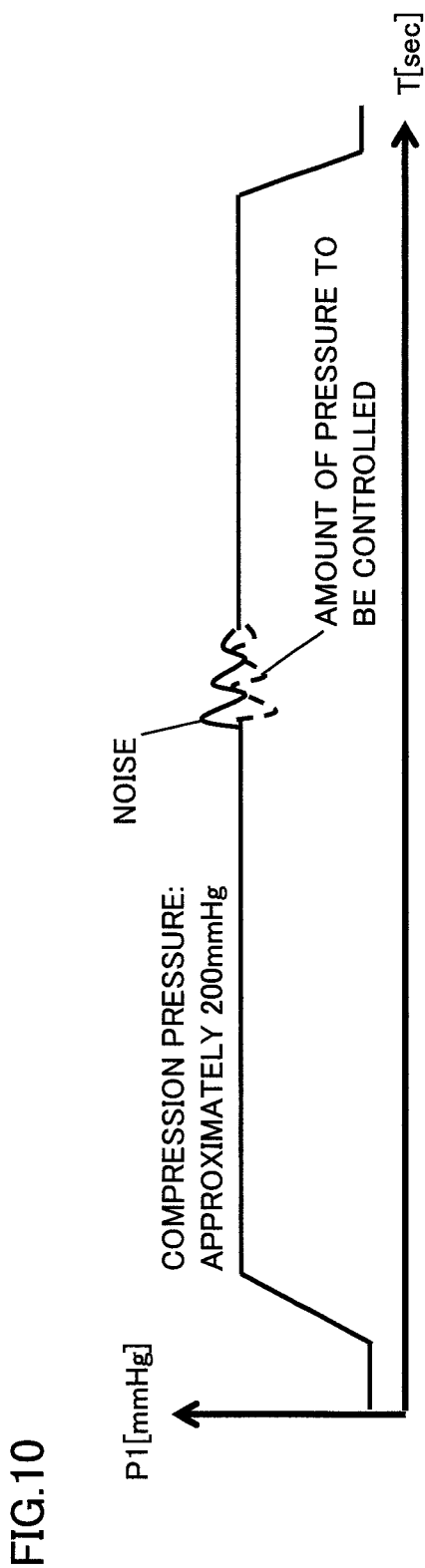
FIG. 10 shows changes with time in pressure in a curler-compressing air bag during the measuring operation at the pulse wave meter.

FIG. 9 is a flow chart showing a measuring operation including a pressure adjusting step according to the modification at pulse wave meter 1. FIG. 10 shows changes with time in pressure P1 in air bag 8 during the measuring operation at pulse wave meter 1. In the measuring operation shown in FIG. 9, although not shown in FIG. 10, changes with time in pressure P2 in air bag 13B and changes with time in pressure P3 in air bag 13A are similar to those shown at (B) and (C) in FIG. 8, respectively.

With reference to FIG. 9, the measuring operation according to the modification includes steps S31, S33 and S37 in addition to the measuring operation shown in FIG. 7. More specifically, with reference to FIG. 9, after terminating the pressurization of air bag 13A at step S13 to keep the pressure, CPU 40 causes the pressure in air bag 8 to be measured based on the pressure signal from pressure sensor 33 (step S31). CPU 40 causes the obtained pressure in air bag 8 to be compared with the pressure in air bag 8 controlled to be kept at step S5, so that changes in pressure in air bag 8 are detected (step S33). As a result, when the occurrence of changes in pressure is detected (YES at step S33), CPU 40 outputs a control signal to air system 30 to adjust the pressure in air bag 8 (step S35). Herein, an adjusting technique is not limited to a particular technique. Preferably, an adjustment of canceling out the occurred noise is performed. As a specific technique, control is exerted such that the degree of the occurred noise, that is, a difference from the pressure in air bag 8 controlled to be kept is obtained by the comparison at step S33, and a pressure is applied or reduced by the same difference in pressure such that the noise is canceled out. Then, CPU 40 causes a pulse wave to be measured (step S15). The above-described steps S31 and S33 are performed until the pulse wave measurement at step S15 is completed (YES at step S37).

In addition to configuring pulse wave meter 1 according to the present embodiment to include member 13C, performing the measuring operation including the pressure adjusting step according to the modification allows a more precise pulse wave to be measured using pulse wave meter 1.

Second Embodiment

Figure 11:
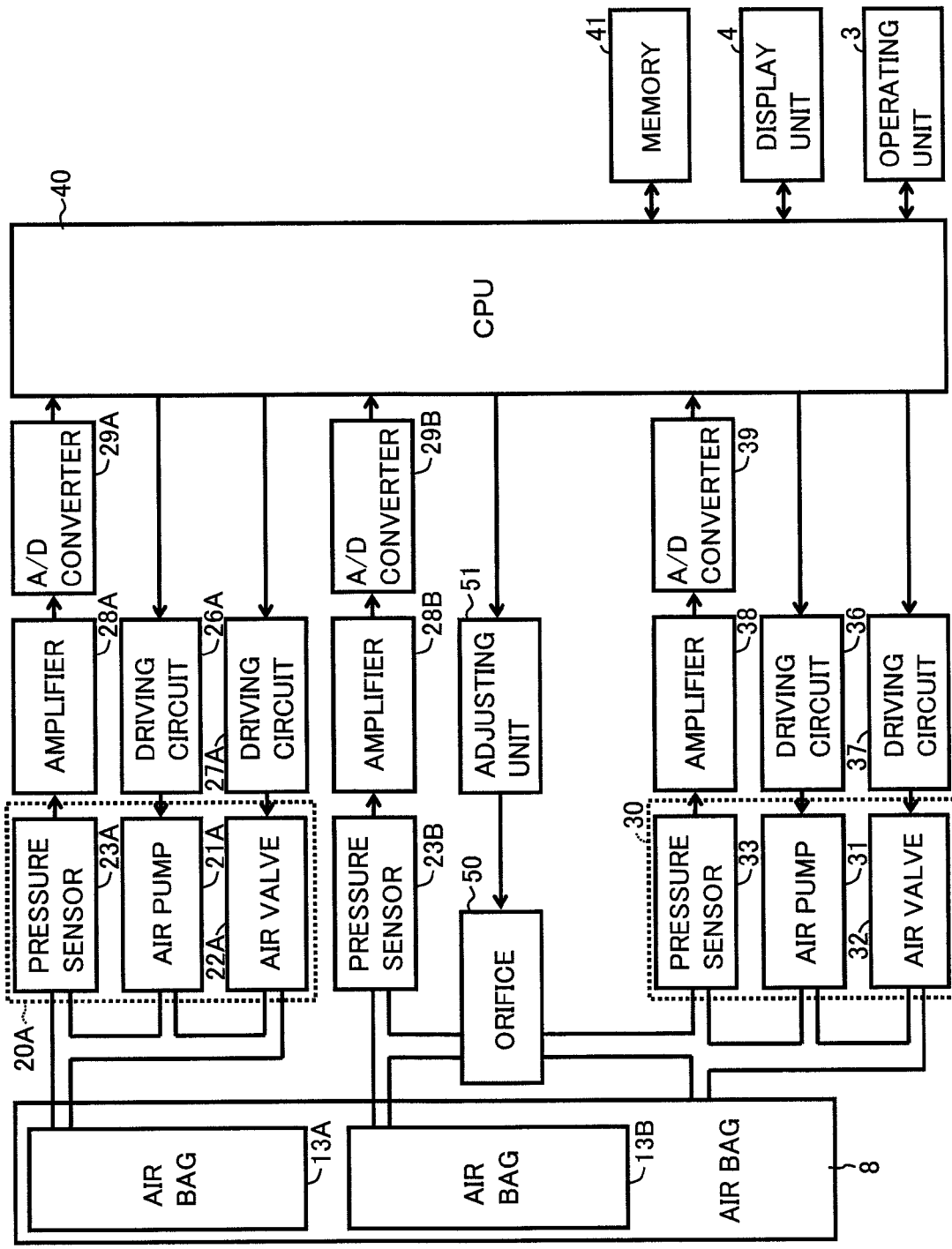
FIG. 11 is a functional block diagram of a pulse wave meter according to a second embodiment.

FIG. 11 is a functional block diagram of pulse wave meter 1 according to the second embodiment. As compared to pulse wave meter 1 according to the first embodiment shown in FIG. 5, pulse wave meter 1 according to the second embodiment does not include air pump 21B, air valve 22B, driving circuit 26B, and driving circuit 27B, but includes an orifice 50 instead.

In pulse wave meter 1 according to the second embodiment, the air tube from air bag 13B and the air tube from air bag 8 are connected to each other with orifice 50 interposed therebetween. Orifice 50 allows air flowing between air bags 8 and 13B to be a predetermined amount. Preferably, this predetermined amount is determined previously at such an amount that the pressure in air bag 13B becomes equal to the pressure in air bag 8. Alternatively, the amount of airflow through orifice 50 may be variable, and an adjusting unit 51 may further be provided as shown in FIG. 11, so that adjusting unit 51 adjusts the above-mentioned amount of airflow through orifice 50 based on a control signal from CPU 40. In the present invention, orifice 50 is not limited to a particular configuration. Orifice 50 may be configured, for example, to include a flow channel between air bags 8 and 13B and a valve for blocking the flow channel, wherein the degree of opening the valve is variable. In this case, adjusting unit 51 adjusts the degree of opening of the valve in accordance with a control signal from CPU 40 to adjust the amount of airflow between air bags 8 and 13B such that the pressure in air bag 13B becomes equal to the pressure in air bag 8. CPU 40 causes the pressure in air bag 13B and the pressure in air bag 8 to be monitored based on the pressure signal from pressure sensor 23B and the pressure signal from pressure sensor 33 to determine the above-mentioned amount of airflow such that these pressures are equal, and outputs a control signal to adjusting unit 51.

Moreover, propagation of vibrations of a predetermined frequency component from air bag 8 to air bag 13B is suppressed (preferably, interrupted) by resonating air which is a fluid in orifice 50 at a predetermined frequency, or the like. By equalizing the above-mentioned predetermined frequency with a frequency of a pulse wave, orifice 50 suppresses (preferably, interrupts) propagation of vibrations of a frequency component in the pulse wave from air bag 8 to air bag 13B.

In pulse wave meter 1 according to the second embodiment, when air bag 8 is pressurized by air system 30 at the above-described step S3 in the measuring operation shown in FIG. 7, air bag 13B is also pressurized through orifice 50 so as to be equal in pressure to air bag 8. Then, when the pressure in air bag 8 is maintained at the predetermined pressure at the above-described step S5, the pressure in air bag 13B is also maintained at the predetermined pressure equal to the pressure in air bag 8. Therefore, in pulse wave meter 1 according to the second embodiment, steps S7 and S9 in the measuring operation shown in FIG. 7 are not performed. Further, at this stage, since orifice 50 functions as described earlier, propagation of vibrations from air bag 8 to air bag 13B is suppressed (preferably, interrupted).

With pulse wave meter 1 according to the second embodiment configured as described above, air systems 30 and 20B share an air pump and an air valve. This allows reduction in the number of components as compared to the pulse wave meter according to the first embodiment while suppressing propagation of vibrations from air bag 8 to air bag 13B.

It is to be noted that, similarly to the second embodiment, the air tube from air bag 13B may be connected to the air tube from air bag 8 with orifice 50 interposed therebetween in the third and fourth embodiments which will be described later. Such a configuration similarly enables reduction in the number of components while suppressing propagation of vibrations from air bag 8 to air bag 13B.

Third Embodiment

In pulse wave meter 1 according to the first and second embodiments, air bag 8 is located at the outer circumferential side of curler 10 that covers both of air bags 13A and 13B integrally, and pressurizes the outer circumferential surface of curler 10 toward the inner side, so that air bags 13A and 13B are pressed against the living body from the outer circumferential side of curler 10. However, a compression mechanism for pressing air bags 13A and 13B against the living body from the outer circumferential side of curler 10 is not limited to an air bag which is a fluid bag, but may be embodied by another member that can press the outer circumferential surface of curler 10 evenly toward the inner side. As an example, pulse wave meter 1 according to the third embodiment employs an artificial muscle.

Figure 12:
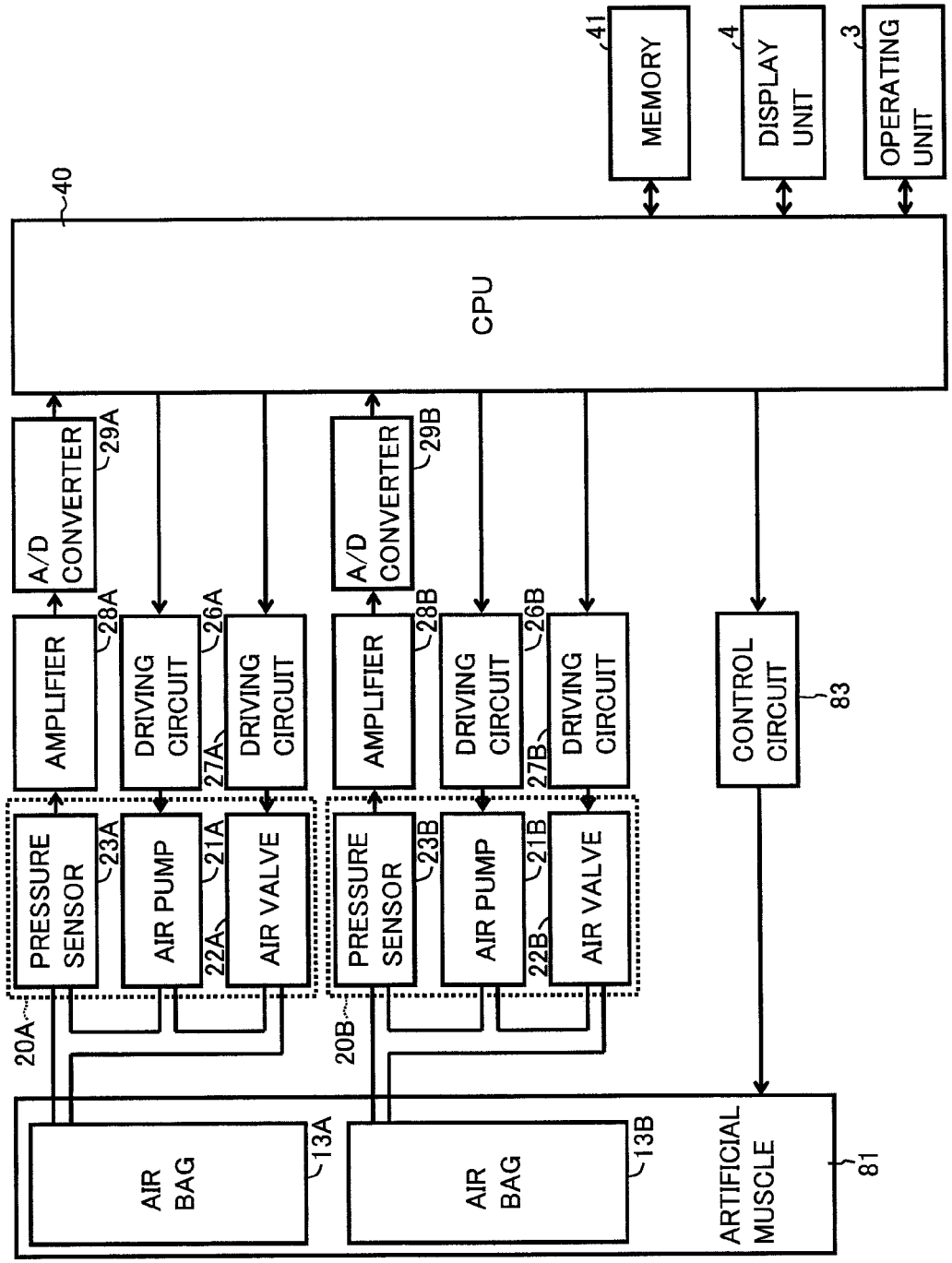
FIG. 12 is a functional block diagram of a pulse wave meter according to a third embodiment.

FIG. 12 is a functional block diagram of pulse wave meter 1 according to the third embodiment. Pulse wave meter 1 according to the third embodiment includes an artificial muscle 81 for pressurizing the curler instead of air bag 8, and also includes a control circuit 83 for controlling the artificial muscle instead of the respective components such as air system 30 for controlling the pressure in air bag 8. Artificial muscle 81 is a kind of actuator, made of a material such as an ion-conductive polymeric gel. Based on a control signal from CPU 40, control circuit 83 generates a signal for operating artificial muscle 81 for output to artificial muscle 81. Artificial muscle 81 generates power from electric energy based on the signal from control circuit 83 to press the outer circumferential surface of curler 10 toward the inner side.

Figure 13:
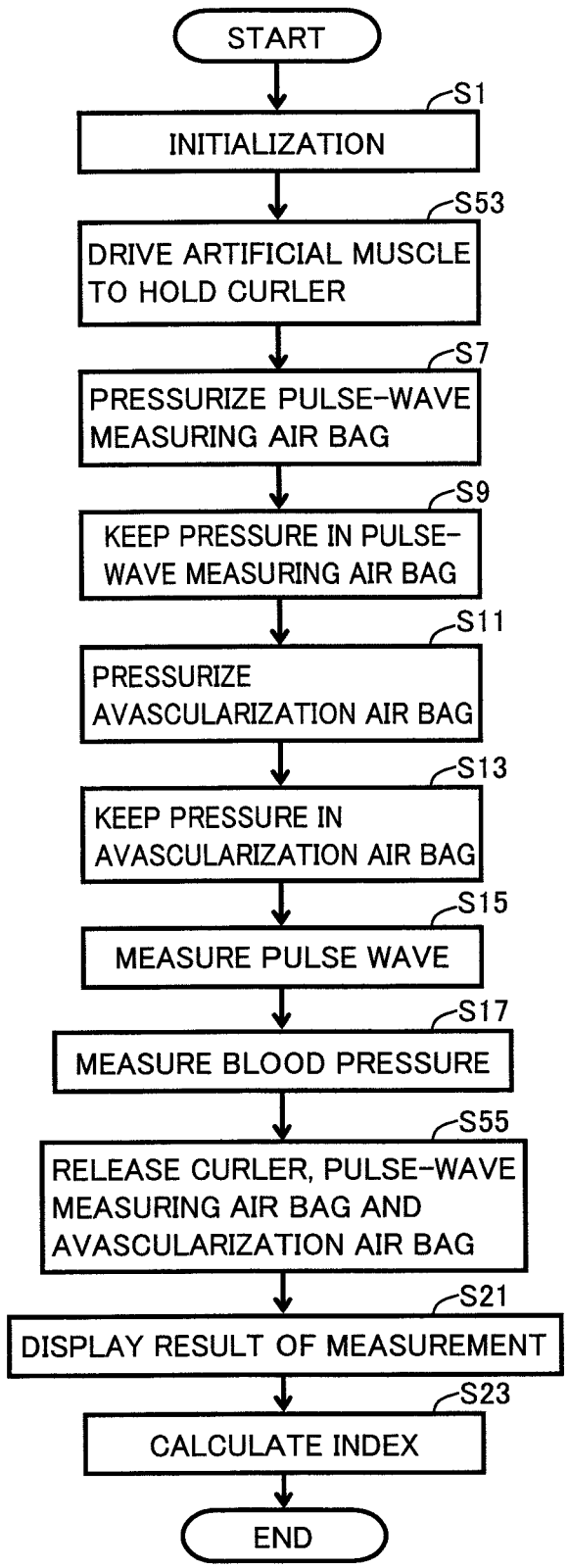
FIG. 13 is a flow chart showing a measuring operation at the pulse wave meter according to the third embodiment.

FIG. 13 is a flow chart showing a measuring operation at pulse wave meter 1 according to the third embodiment. In the measuring operation shown in FIG. 13, a step S53 is performed instead of the above-described steps S3 and S5 in the measuring operation shown in FIG. 7 at which air bag 8 is pressurized to be maintained at a predetermined pressure. At step S53, CPU 40 outputs a control signal to control circuit 83 to drive artificial muscle 81 such that curler 10 presses air bags 13A and 13B against the living body with a predetermined pressure force, thereby holding curler 10. Moreover, instead of the aforementioned step S19, at step S55, the pressures in air bags 13A and 13B are released to atmospheric pressure, and curler 10 is released from holding.

As described above, the pulse wave meter equipped with the arteriosclerosis degree judgment device according to the present invention can also be achieved when the compression mechanism for pressing air bags 13A and 13B against the living body from the outer circumferential side of curler 10 is embodied by a member other than an air bag.

Fourth Embodiment

As described earlier, in pulse wave meter 1 according to the first to third embodiments, a pulse wave is measured based on changes in internal pressure in air bag 13B, and a blood pressure is calculated based on changes in internal pressure in air bag 13A. Accordingly, air bag 13A needs to have a dimension along an artery for ensuring an artery length necessary for blood pressure measurement (e.g., approximately 12 cm). As a result, a dimension along an artery of air bag 8 needs to be at least the sum of the above-mentioned dimension of air bag 13A and a dimension along an artery of air bag 13B for ensuring an artery length necessary for pulse wave measurement.

Herein, as described earlier, air bag 8 is located at the outer circumferential sides of air bags 13A and 13B, and member 13C disposed between air bags 8 and 13B is not present between air bags 8 and 13A, so that changes in internal pressure in air bag 13A propagate to air bag 8. Accordingly, pulse wave meter 1 may be configured such that a blood pressure is calculated based on changes in internal pressure in air bag 8, instead of changes in internal pressure in air bag 13A.

Figure 14:
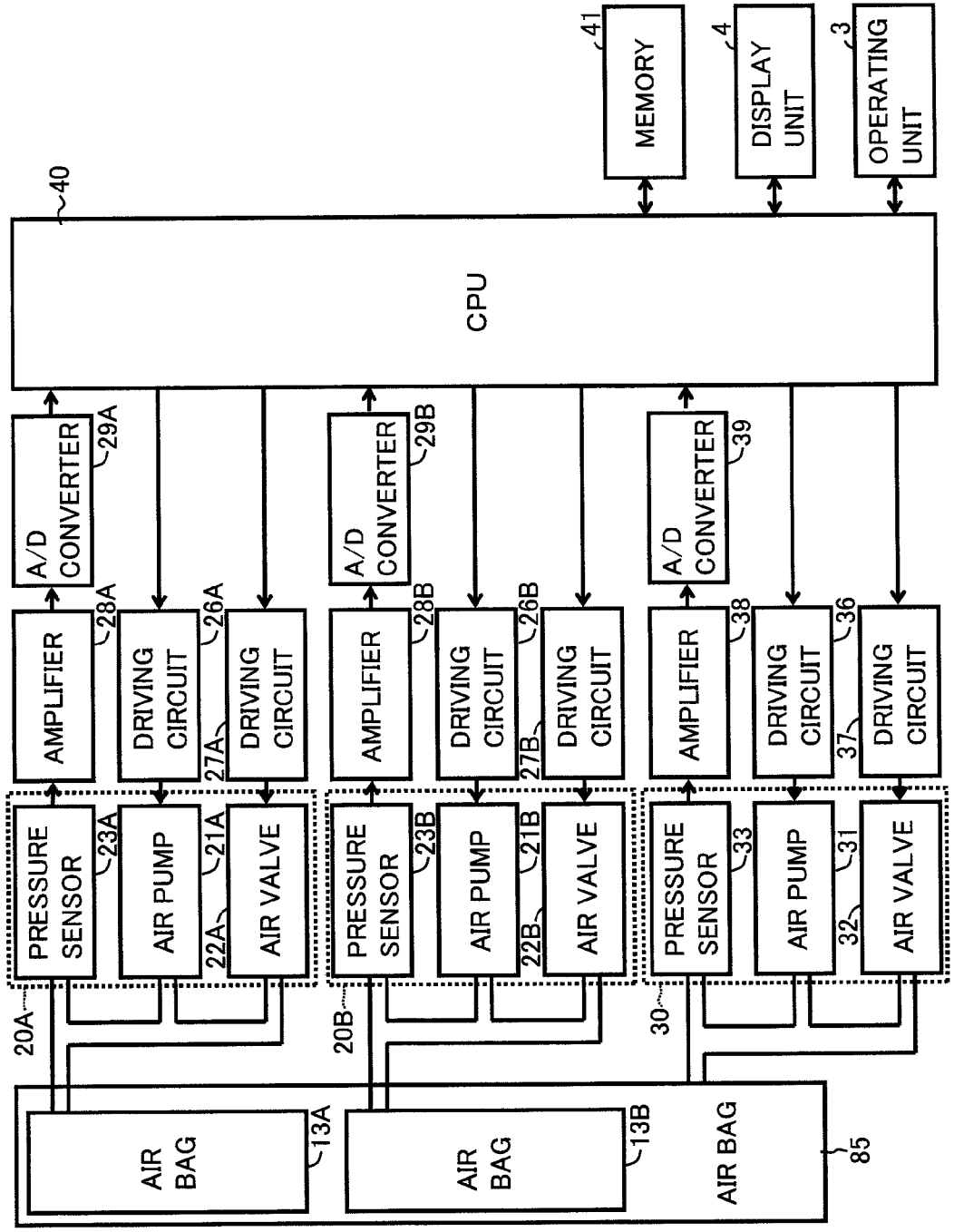
FIG. 14 is a functional block diagram of a pulse wave meter according to a fourth embodiment.

FIG. 14 is a functional block diagram of pulse wave meter 1 according to the fourth embodiment. Pulse wave meter 1 according to the fourth embodiment includes an air bag 85 instead of air bag 8, and the respective components such as air system 30 for controlling the pressure in air bag 8 are used for controlling the pressure in air bag 85. It is to be noted that pulse wave meter 1 according to the fourth embodiment does not include curler 10, and inflation of air bag 85 located at the outer circumferential sides of air bags 13A and 13B allows air bag 13A and air bag 13B (with member 13C interposed therebetween) to be pressed against the living body.

Air bags 13A and 8 may be integrated such that air bag 13A presses the living body and air bag 13B (with member 13C interposed therebetween).

The configuration that air bag 85 is provided instead of air bag 8 and the configuration that air bags 13A and 8 are integrated can be collectively referred to as a configuration that a compression member for compressing air bags 13A and 13B is also used as air bag 13A.

By providing pulse wave meter 1 according to the fourth embodiment with the configuration that the compression member for compressing air bags 13A and 13B is also used as air bag 13A, the above-mentioned dimension along an artery of the compression member can be made equal to the dimension along an artery for ensuring an artery length necessary for blood pressure measurement, that is, the dimension along an artery of air bag 13A. Accordingly, measuring unit 5 can be reduced in size, leading to size reduction of the whole device.

The measuring operation at pulse wave meter 1 can also be embodied as shown in FIG. 15 instead of the operation shown in FIG. 7. Herein, the measuring operation shown in the flow chart of FIG. 15 represents the measuring operation at pulse wave meter 1 according to the fourth embodiment. However, the measuring operation is not limited to the fourth embodiment, but may be performed at pulse wave meter 1 according to any of the first to third embodiments.

With reference to FIG. 15, in the measuring operation shown in the flow chart of FIG. 15, after the initialization at the above-described step S1 in the measuring operation shown in FIG. 7, at step S71, a selection between a mode of measuring a pulse wave and a mode of measuring a blood pressure alone is received at operating unit 3 to separate steps to be performed thereafter. Upon receipt of a selection of the mode of measuring a pulse wave at step S71 (YES at step S71), CPU 40 causes the pressure in air bag 85 to be adjusted similarly to the adjustment of pressure in air bag 8 at the above-described steps S3 and S5. Subsequently, steps similar to those in the measuring operation shown in FIG. 7 are performed.

Upon receipt of a selection of the mode of measuring a blood pressure alone at step S71 (NO at step S71), CPU 40 causes, at next step S81, air bag 85 to be pressurized similarly to the above-described step S73, and then detects an artery pressure pulse wave based on the pressure signal from pressure sensor 33 while gradually reducing the pressure in air bag 85. Then, blood pressure values (systolic blood pressure (SYS) and diastolic blood pressure (DIA)) are calculated based on detected data of the artery pressure pulse wave (step S83). That is, the pulse wave is measured based on changes in internal pressure in air bag 85 to which changes in internal pressure in air bag 13A have propagated. Then, CPU 40 causes the pressure in air bag 85 to be released to atmospheric pressure (step S85), and causes display unit 4 provided on base 2 to display the calculated systolic blood pressure (SYS) and diastolic blood pressure (MA), so that the result of measurement is displayed (step S87).

By performing the above-described measuring operation at pulse wave meter 1, pulse wave meter 1 can be used not only for measuring a pulse wave to attain an index for judging a degree of arteriosclerosis, but also as a blood pressure meter. When wishing to measure a blood pressure alone, a blood pressure value can be obtained quickly in a simple operation.

Although the present invention has been described and illustrated in detail, it is clearly understood that the same is by way of illustration and example only and is not to be taken by way of limitation, the scope of the present invention being interpreted by the terms of the appended claims.

The invention claimed is:

1. An arteriosclerosis degree judgment device comprising:
a first fluid bag to be wrapped around a measurement site at a central side thereof and a second fluid bag to be wrapped around the measurement site at a peripheral side thereof;
a compression member located at outer circumferential sides of both of said first fluid bag and said second fluid bag to oppose to said measurement site, for integrally covering both of said first fluid bag and said second fluid bag;
a first sensor for measuring an internal pressure in said first fluid bag;
an adjustment unit for adjusting a pressure force of said compression member;
a detection unit for detecting a pulse wave at said measurement site based on a change in the internal pressure in said first fluid bag; and
a calculation unit for analyzing said pulse wave to calculate an index for judging a degree of arteriosclerosis,
wherein said adjustment unit causes said compression member to pressurize both of said first fluid bag and said second fluid bag so as to be compressed against said measurement site, said first fluid bag and said second fluid bag being pressed against said measurement site with a certain pressure force, and
wherein said detection unit detects the pulse wave at said measurement site based on the change in the internal pressure in said first fluid bag while being pressed against said measurement site with said certain pressure force,
wherein said compression member is a third fluid bag, and
wherein said adjustment unit detects vibration in said third fluid bag and actively exerts control for adjusting an internal pressure in said third fluid bag in accordance with the vibration of said third fluid bag serving as said compression member to actively cancel out said vibration.

2. The arteriosclerosis degree judgment device according to claim 1, wherein said detection unit detects the pulse wave at said measurement site based on the change in the internal pressure in said first fluid bag with said second fluid bag being pressed against said measurement site to provide avascularization.

3. The arteriosclerosis degree judgment device according to claim 1, further comprising a suppression member disposed between said first fluid bag and said compression member for suppressing propagation of a vibration of said compression member to said first fluid bag.

4. The arteriosclerosis degree judgment device according to claim 1,
wherein said first fluid bag and said third fluid bag serving as said compression member are connected to each other with an orifice interposed therebetween, and
wherein said orifice suppresses propagation of a vibration of said third fluid bag to said first fluid bag.

5. The arteriosclerosis degree judgment device according to claim 4, further comprising an orifice adjusting unit for adjusting an amount of flow of fluid through said orifice between said first fluid bag and said third fluid bag, said orifice adjusting unit adjusting said amount of flow such that said first fluid bag has a constant pressure.

6. The arteriosclerosis degree judgment device according to claim 1,
wherein said compression member is an artificial muscle member that produces power from an electrical signal, and
wherein said adjustment unit outputs said electrical signal to said artificial muscle member serving as said compression member to adjust the pressure force.

7. The arteriosclerosis degree judgment device according to claim 1, further comprising:
a second sensor for measuring an internal pressure in said second fluid bag,
wherein said calculation unit calculates a blood pressure value based on a change in the internal pressure in said second fluid bag.

* * * * *